(12) United States Patent
Mantle

(10) Patent No.: US 7,842,002 B2
(45) Date of Patent: Nov. 30, 2010

(54) DEVICE FOR THE EXTRAVASCULAR RECIRCULATION OF LIQUID IN BODY CAVITIES

(76) Inventor: Ross E. Mantle, 96 Trump Avenue, Ottawa, Ontario (CA) K2C 4A2

( * ) Notice: Subject to any disclaimer, the term of this patent is extended or adjusted under 35 U.S.C. 154(b) by 1012 days.

(21) Appl. No.: 10/523,857

(22) PCT Filed: Nov. 12, 2003

(86) PCT No.: PCT/CA03/01732

§ 371 (c)(1), (2), (4) Date: May 11, 2005

(87) PCT Pub. No.: WO2004/043313

PCT Pub. Date: May 27, 2004

(65) Prior Publication Data

US 2006/0161107 A1    Jul. 20, 2006

(30) Foreign Application Priority Data

Nov. 12, 2002   (CA) .................................. 2411569

(51) Int. Cl.
*A61M 37/00*   (2006.01)
(52) U.S. Cl. ..................... 604/6.11; 604/6.05
(58) Field of Classification Search ................ 604/4.01, 604/6.09, 6.15, 6.16, 317, 319, 6.11, 6.13; 422/44–48
See application file for complete search history.

(56) References Cited

U.S. PATENT DOCUMENTS

| | | | |
|---|---|---|---|
| 3,927,980 A * | 12/1975 | Leonard | 422/48 |
| 4,445,500 A | 5/1984 | Osterholm | |
| 4,450,841 A * | 5/1984 | Osterholm | 600/363 |
| 5,122,267 A | 6/1992 | Giovanetti et al. | |
| 5,141,493 A | 8/1992 | Jacobsen et al. | |
| 5,149,321 A * | 9/1992 | Klatz et al. | 604/500 |
| 5,380,160 A | 1/1995 | Chen | |
| 5,554,280 A | 9/1996 | Loehr | |
| 5,562,821 A * | 10/1996 | Gutierrez-Collazo | 210/167.26 |
| 5,665,227 A | 9/1997 | Watt | |
| 6,254,567 B1 | 7/2001 | Treu et al. | |
| 6,379,331 B2 | 4/2002 | Barbut et al. | |
| 6,409,699 B1 | 6/2002 | Ash | |
| 6,436,295 B2 | 8/2002 | Kim | |
| 6,497,721 B2 * | 12/2002 | Ginsburg et al. | 607/106 |
| 6,743,218 B2 * | 6/2004 | Maginot et al. | 604/510 |

OTHER PUBLICATIONS

"Epidural Cooling for Regional Spinal Cord. Hypothermia During Thoracoabdominal Aneurysm Repair", Davison JK, Cambria RP, Vierra DJ, Columbia MA, Koustas G., J. Vasc. Surg, Aug. 20, 1994 (2) 304-10 Abstract Only.

* cited by examiner

*Primary Examiner*—Tatyana Zalukaeva
*Assistant Examiner*—Philip R Wiest
(74) *Attorney, Agent, or Firm*—Shay Glenn LLP

(57) ABSTRACT

Biocompatible liquid is pumped into a body cavity (eg. subarachnoid space, peritoneum, mediastinum, pleural space) by means of one pump and removed from it by means a second pump, preferably via a double-barreled catheter is used for insertion and removal of the liquid. An optional secondary catheter removes liquid from a distal area of the body cavity. Temperature and pressure are sensed within the cavity and can be controlled by adjusting liquid flow rates. While outside the body, the liquid can be ultraviolet-sterilized, foam fractionated to remove contaminants, oxygenated and pH balanced, cooled or warmed, and augmented with exogenous liquid that may contain drugs.

20 Claims, 4 Drawing Sheets

Flow: 44 mL/min

Flow: 150 mL/min

Flow: 168 mL/min

DEVICE FOR THE EXTRAVASCULAR RECIRCULATION OF LIQUID IN BODY CAVITIES

This application is a United States National Entry of Patent Co-operation Treaty Application PCT/CA03/01732, filed Nov. 12, 2003, claiming priority from Canadian patent application 2,411,569, filed Nov. 12, 2002.

FIELD OF INVENTION

This invention relates to processes and devices for automated extracorporeal recirculation and chemical manipulation of biological and biocompatible liquids such as for example cerebrospinal fluid, artificial cerebrospinal fluid, saline, and Ringer's lactate in body cavities for the purposes of prevention or treatment of a variety of disorders.

BACKGROUND OF THE INVENTION

A number of clinical situations exist in medicine in which automated control of the temperature, pressure and chemistry of liquid within a body cavity are likely to be therapeutically useful. These include:

1. Traumatic or ischemic brain and spinal cord injuries, in which temperatures below normal and control of pressure may improve outcome.
2. Hemorrhage in the regions of the brain and spinal cord, in which removal of blood may improve outcome.
3. Infection in the regions of the brain and spinal cord, in which addition of antibiotics or antivirals to the CSF spaces may be beneficial. Hypothermia, hyperthermia, or oscillation between hypothermia and hyperthermia, pressure control, and removal of infectious organisms (pus) and inflammatory mediators from the cerebrospinal fluid (CSF) may also be beneficial.
4. Brain edema related to liver failure, in which hypothermia has been shown to be beneficial.
5. Malignancy in the regions of the brain and spinal cord, in which hyperthermia has been shown to increase the efficacy of chemotherapy and radiation in the treatment of glioblastoma multiforme, the most common, and usually fatal, form of brain cancer.
6. Infection in the region of other body cavities, including peritonitis, pleuritis, and mediastinitis, in which the continuous delivery of antibiotic, antiviral, or related therapies under controlled temperature and pressure could be useful. Such therapies have been delivered into the peritoneum and other cavities, but without feedback control of temperature or pressure.
7. Malignancy in the region of body cavities, including the peritoneum, pelvis, mediastinum, and pleural space, in which hyperthermia and/or the local delivery of chemotherapeutic agents have shown greater effectiveness than conventional therapies in some studies.
8. Ischemia of the intestine or colon, in which hypothermia might protect the tissues from ischemic damage. Such protection may apply in other organs subject to ischemia, such as the heart.
9. Surgery involving any of the above regions, in which local hypothermia can decrease the metabolic demands of tissues, resulting in decreased susceptibility to injury and decreased bleeding due to lower blood flow, and post-operative adverse events in such regions.

Hypothermia in Brain and Spinal Cord Injuries

The protective effects of hypothermia applied during injuries has been extensively documented, and is currently in use intraoperatively in certain forms of brain surgery and cardiac surgery.

Hypothermia has been shown to be effective when applied contemporaneously with the injury in both brain trauma and brain ischemia in animals in a large number of studies. Disappointing early results with delayed hypothermia, and the resultant widespread notion of a narrow 'therapeutic window' dampened enthusiasm in this area for many years. Recent reports suggest that much longer hypothermic times than were previously contemplated can compensate for delays in treatment and produce outcomes comparable to contemporaneous hypothermia.

However, some studies indicate that the systemic complications of prolonged whole-body hypothermia (also called whole body cooling, or WBC) are a major barrier to the effectiveness of this therapy in either stroke or trauma in humans. As a result, some investigators have focused on a human strategy of selective brain cooling (also called SBC). Unfortunately, SBC is very difficult to achieve in large animals such as humans. Compared with smaller animals, the human head has a low surface area-to-volume ratio and a high degree of thermal inertia. The human brain is insulated from the surface of the head by approximately 2.5 cm of highly vascular scalp, bone, meninges and cerebrospinal fluid (CSF). In addition, the brain receives constant thermal input in the form of 20% of the cardiac output, or 1 L/min of blood at 37° C. Because of this, reduction of the surface temperature of the human head has been shown to be ineffective as a method of SBC.

An alternative to surface cooling is intra-arterial cooling using either bypass-cooled blood or intra-arterial cooling probes. Intra-arterial approaches suffer from the major inherent risk of endovascular instrumentation of the cranial arteries; that of precipitating stroke. To minimize this risk, such instrumentation is normally done under full dose heparin anticoagulation, which may be contraindicated in both trauma and stroke due to the risk of bleeding.

It has been taught to withdraw cerebrospinal fluid (CSF), cool it, and return the cooled CSF to a patient.

U.S. Pat. No. 4,904,237 (Janese, 1990) discloses a CSF exchange system which removes CSF from the lumbar cistern, filters out blood contaminants, cools, pH adjusts and performs diagnostic measurements, then returns the CSF to the lumbar cistern by reversal of flow using a single reciprocating pump. This system seems intended primarily for the removal of subarachnoid blood from the CSF in the context of subarachnoid hemorrhage. In the preferred embodiment, 10 ml of CSF are exchanged in 25 s cycles, giving a flow rate of 24 ml/min. If the temperature of the returned CSF is at 4° C., this flow rate may not be adequate to achieve significant cooling in the spinal cord, where published flows of approximately 30 ml/min were required in a human trial (Davison et al, 1994).

U.S. Pat. No. 6,379,331 (Barbut, 2002) discloses another medical device for intrathecal cooling of the spinal cord in which separate inflow and outflow catheters are inserted into the CSF spaces of the spinal cord such that their tips are at the extremities of the cavity to be cooled. CSF is extracted from one catheter, cooled, and returned to the second catheter by means of a single pump without automated feedback control. The flow rate of the single pump is adjusted to keep intraspinal pressure (as estimated from the pressure of the extracorporeal fluid, and not from measurement within the cavity) below a safe level. This system is intended primarily for the special case of intraoperative spinal cord cooling in the context of abdominal aortic aneurysm surgery and provides no means of continued cooling over 24 h or more, as required for delayed hypothermia to be effective. Alternate placement of one of the catheters into the lateral ventricle of the brain is disclosed as a method of cooling the brain, although practical brain cooling would seem unlikely due to flow rate limitations. A difficulty with any catheter arrangement in which the catheter tips are separated in space is that pressure differentials may occur between the inflow and outflow regions at higher flow rates. Hence, the maximal flow is limited by the maximal safe pressure in the region of the inflow catheter, where pressure is high, and minimal safe pressure in the region of the outflow catheter, where pressure is low. Placement of two catheters in the brain ventriclular system such that their tips are relatively close together suffers from the disadvantage of having to pierce the brain twice, doubling the risk of intraparenchymal hemorrhage due to catheter placement.

U.S. Pat. No. 4,445,500 (Osterholm) discloses a treatment for stroke involving the recirculation of an oxygenated perfluorocarbon emulsion in the subarachnoid (CSF) space. This system is intended to counteract ischemic injuries of the central nervous system by providing sufficient oxygen in the perfusate to allow continued tissue metabolism in the face of insufficient blood flow. The system depends on an involved process for the manufacture and maintenance of the perfluorocarbon emulsion, which is a fluid whose biocompatibility would need to be established. As in the previously discussed patent, a single pump is again used for circulation of the fluid within the subarachnoid space, which precludes active pressure modulation, and the inflow and outflow catheters are separated. The low flow rates possible under this configuration (<60 ml/min) are disclosed as sufficient for adequate brain oxygentation with the emulsion used. Intracranial pressure measurements are made by means of a double lumen catheter in which one lumen is devoted to pressure measurements. The infusion rate into the brain is adjusted manually to keep the pressure below a safe limit. The temperature of the emulsion may be adjusted extracorporeally, but no measurements of temperature are made within the CNS. Together with the low flow rates, this would seem to preclude practical and precise therapeutic temperature modulation. Precise control of temperature is required in hypothermic therapy, particularly during the dangerous rewarming stage, and to an even greater extent in therapeutic hyperthermia, in which overheating can severely damage normal tissue. Finally, with regard to the removal of contaminants, the Osterholm system calls for microfiltration of the emulsion as a means of removing bacteria, but discloses no means of removal of other contaminants, such as proteins or blood products.

Liquid in Non-CNS Body Cavities

Devices for recirculation of liquids in the peritoneal cavity have been disclosed in, for example, U.S. Pat. Nos. 6,254, 567, 6,409,699, and 5,141,493. These devices are dialysate circulators for the purpose of continuous flow-through intraperitoneal dialysis (CFPD) used in the treatment of kidney or liver failure. Many of these designs incorporate a heater whose purpose is to warm the dialysate to body temperature before it enters the body, but therapeutic temperature modulation is not encompassed. They generally feature a means of maintaining constant pressure of the dialysate fluid extracorporeally, but do not accomplish pressure modulation within the cavity by use of independent inflow and outflow pumps. These devices are also not intended for the delivery of drugs or the removal of contaminants such as blood or pus.

Foam Fractionation

Foam fractionation is a technique for the removal of proteins and other contaminants from a liquid. This technique is used in marine aquaculture, where it is commonly known as 'protein skimming'. Dissolved amphipathic (partly water soluble and partly non-water soluble) molecules such as proteins tend to accumulate at an air/water interface since part of the molecule is more stable when dissolved in aqueous solution and part is more stable in air. Such molecules can be removed with high efficiency from liquids with favorable physical properties by saturation of the solution with fine bubbles. The bubbles accumulate proteins at the air/water interface and the resulting foam rises to the top of the liquid, where it may be collected or skimmed off. As an additional benefit, the intimate contact of air or of a gas mixture containing oxygen can oxygenate the liquid. Contact of an oxygen-carbon dioxide gas mixture with a bicarbonate-buffered solution, for example, can both oxygenate and pH balance the solution. U.S. Pat. Nos. 6,436,295, 5,562,821, 5,554,280, 5,122,267, 5,665,227, and 5,380,160, for example, describe devices for foam fractionation in marine aquariums. Foam fractionation is also used in the purification of proteins and drugs in the pharmaceutical industry. Foam fractionation has apparently not been disclosed for use in the purification of a bulk liquid for recirculation within a body cavity.

SUMMARY OF THE INVENTION

A process and device are disclosed for liquid recirculation to and from a body cavity (eg. subarachnoid space, cerebral ventricular system, mediastinum, pleural space, peritoneum). Preferably a two channel catheter is used where one channel inserts liquid and the other removes it. One or more secondary drainage catheters may also be inserted as needed to enhance the distribution of the liquid within the cavity. In a preferred embodiment equipped with automated feedback-controlled pumps and heating/cooling elements, the device allows control of the temperature and pressure of the liquid over short or long time periods (hours to days) according to predetermined protocols. Further preferred embodiments permit manipulation of the liquid, such as dilution with artificial liquids, removal of contaminants by foam fractionation, oxygenation, pH balancing, and addition of chemical agents or drugs.

A process and device for removal of body liquids, treatment of them by foam fractionation and optional other processes, and their return to the body cavity from which they came is also disclosed.

Apparatus for automated regional temperature, pressure and liquid composition control in a body cavity is disclosed using cooling or heating, foam fractionation, and recirculation of a biological or biocompatible liquid to and from the body cavity.

In the preferred embodiment, a single double-barreled catheter is inserted into a body cavity. Liquid is continuously withdrawn from the cavity by means of a first (outflow) pump connected to one barrel (lumen) of the catheter using sterile tubing. At the same time, liquid is continuously added to the cavity by means of a second (inflow) pump connected to the other barrel (lumen) of the catheter using sterile tubing. The catheter incorporates a sensor located along its length (and thermally insulated from it) which is capable of sensing both the temperature and pressure of the interior of the cavity in the vicinity of the catheter shaft.

Liquid pumped out of the outflow barrel of the catheter by means of the outflow pump is conducted via the tubing to a conditioning chamber. Preferably, the liquid is conditioned by irradiation with short wave ultraviolet light to sterilize the liquid. Preferably also, the liquid in the conditioning chamber is also continuously permeated by fine bubbles of gas from a pressurized gas source to entrain contaminants by foam fractionation and to remove them as foam. Fresh liquid is preferably continuously added to the chamber for example by gravity feed from an external reservoir (eg. hanging bag), and the excess liquid is drained into a waste reservoir from an overflow aperture in the chamber. This overflow collects surface foam containing concentrated contaminants extracted by the foam fractionation effect of the bubbles. At the same time, the liquid in the conditioning chamber is cooled by means of refrigeration of the chamber walls or warmed by means of heating of the chamber walls. The temperature of the chamber is measured by means of a temperature sensor in contact with a portion of the chamber, and feedback-controlled by means of closed loop feedback control of a chiller/heater unit.

Liquid is withdrawn from the chamber by means of the inflow pump and conducted to the inflow barrel of the catheter via sterile tubing where it is discharged into the body cavity.

A secondary catheter which drains liquid back to the chamber at a slower rate relative to the primary catheter may be positioned in a distant portion of the body cavity to improve distribution of the recirculated liquid.

At the primary catheter, the flow rates of the inflow and outflow pumps are preferably feedback-regulated based on intra-cavity temperature and pressure information relayed from the sensor in the primary catheter. By appropriate regulation of the inflow and outflow rates, desired temperature and pressures can be achieved within the cavity. Preprogrammed temperature and pressure profiles can be executed over several days by means of an automated computer-based system. Flow in the secondary catheter, if present, is regulated based on information from a sensor capable of measuring the temperature of the liquid removed by this catheter. Greater flow through this catheter can improve the distribution of temperature-controlled liquid to an extremity of a body cavity.

Drugs or other agents may be added to the circulating liquid via the external reservoir. Gaseous exchange between the bubbled gas and the liquid in the chamber can be used to oxygenate, adjust pH, or otherwise condition the liquid while contaminants are removed by foam fractionation and collected as waste.

BRIEF DESCRIPTION OF THE DRAWINGS

The invention will be further described by reference to the drawings, in which.

DETAILED DESCRIPTION OF THE INVENTION AND PREFERRED EMBODIMENTS

Figure 1:
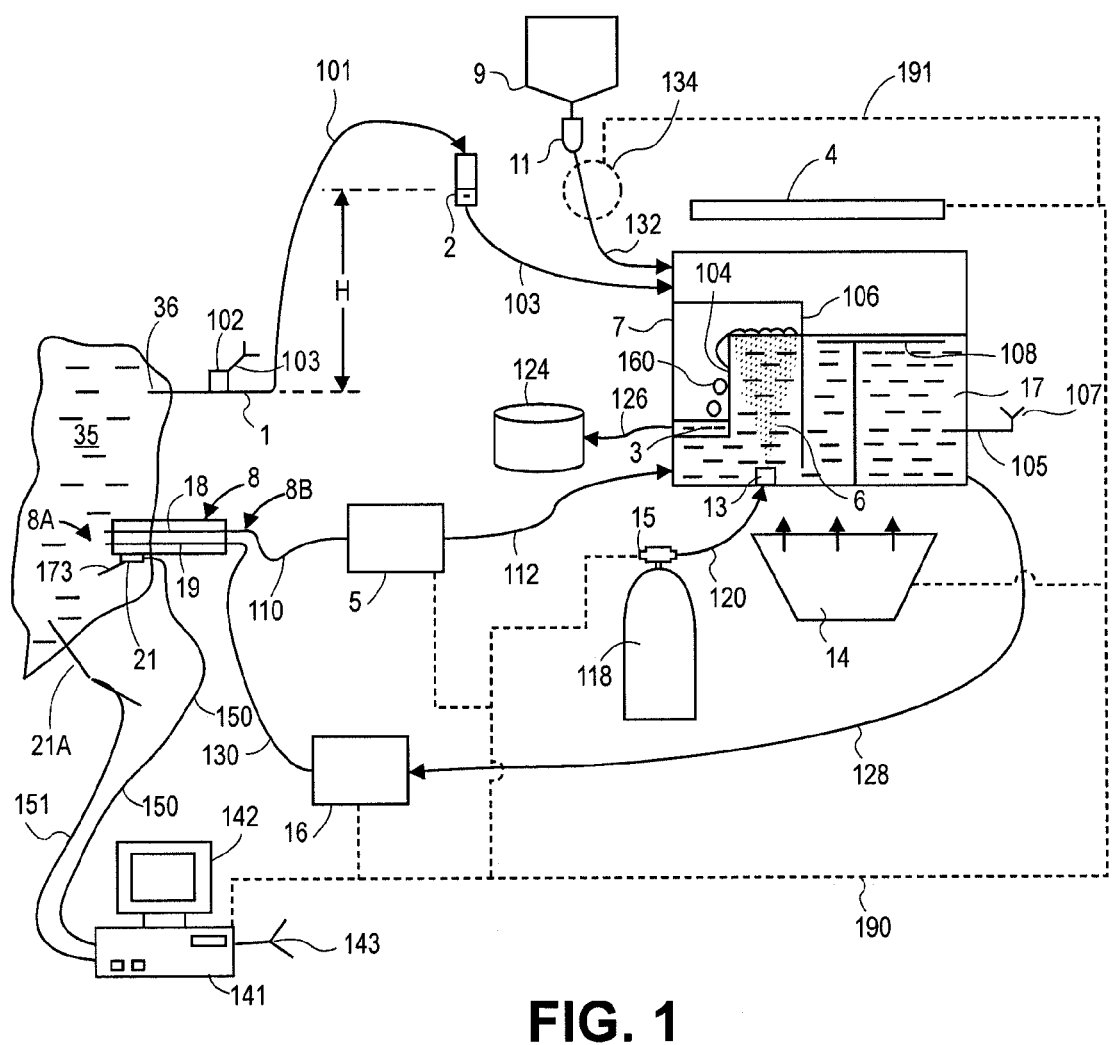
FIG. 1 is a block diagram depicting the main components of a preferred embodiment of the device and their interconnections.

FIG. 1 shows a preferred embodiment in which a body liquid is circulated from a body cavity 35 to one or more conditioning chambers and is then returned to the body cavity. Withdrawal of the liquid and primary return is preferably done by a double-barrelled primary catheter 8, although two separate catheters, one for withdrawal of the liquid and one for its return are within the scope of the invention. Optionally, a secondary catheter 1 is also present to improve distribution of the recirculated liquid to a distal portion of the cavity.

The primary catheter 8 is preferably a cylindrical catheter made of biocompatible material that is divided internally into two lumens 18 and 19. The insertion (also called "distal") end 8A of the catheter has openings to each lumen located near its tip. In the preferred embodiment, the catheter is fabricated from a biocompatible plastic and has a diameter of 5 mm. At the external end (also called the "proximal" end) 8B of the catheter, each lumen is connected separately to tubing. In one embodiment, a sensor package 21 is incorporated into the wall of the catheter such that the sensor package 21 can measure the pressure and temperature of the surrounding tissues. In another embodiment, a sensor package 21A can be separate from the catheter and inserted into the body cavity in a different location. In the preferred embodiment, the pressure-sensitive portion of the sensor package is a miniature 4-wire strain gauge 171 containing a sealed 1 atm pressure reference and connected to an electronic data display and data storage external to the patient. In the preferred embodiment, the temperature-sensing portion of the sensor package is a fine T-type thermocouple wire connected 172, 173 connected to electronic thermocouple display and data and storage external to the patient. The data display and storage are shown schematically as monitor 142 and computer 141. Wires 150 are shown as connecting sensor package 21 to the computer 141, and wires 151 are shown as connecting sensor package 21A to the computer to transfer data from the strain gauge and the thermocouple. However, the data can be relayed by wireless links, as indicated by antenna 143 on the computer, if preferred.

In the preferred embodiment, one end of an optional single-barreled secondary catheter 1 is inserted into a portion of the body cavity 35 distant from catheter 8, as at 36. The other end of catheter 1 is connected via sterile tubing 101 to a burette 2. The height "H" of the burette above the point of entry 36 regulates the pressure head opposing flow through this catheter. The burette may be raised or lowered to adjust flow. Preferably, a sensor capable of measuring the temperature of the liquid withdrawn from catheter 1 is located at some point in the liquid pathway. Conveniently, this sensor is within the catheter, as shown at 102, but it could also be positioned within tubing 101.

The sensor 102 is connected by wires (not shown) or a wireless link (shown by antenna 103) to the computer 141. The liquid is discharged from burette 2 into conditioning chamber 7 by tubing 130. The conditioning chamber is preferably rectangular in shape with a number of internal baffles 104, 106, 108 which slow the passage of liquid through the chamber and promote mixing.

The temperature of liquid in the conditioning chamber is monitored by a thermocouple 105. The temperature sensed is communicated to computer 141 by wireless communication (as shown diagrammatically by antenna 107, which communicates with antenna 143, or by wires (not shown)).

Figure 2A:
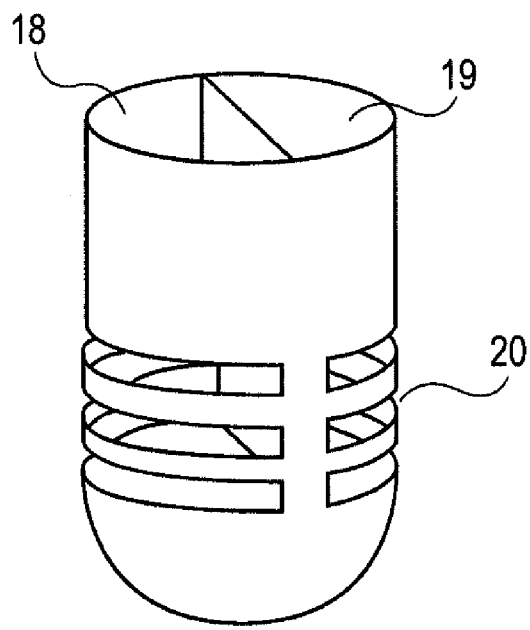
FIG. 2A is an illustration, at a larger scale, of the preferred embodiment of catheter tip (at the intracavity end) for the primary catheter.

The primary catheter 8 runs from an insertion tip 8A within the body to an external tip 8B. Catheter 8 has two lumens, outflow barrel (lumen) 18 and inflow barrel 19 (lumen) (FIG. 2A). Outflow barrel 18 takes liquid from the body, passes it through sterile tubing 110, pump 5 sterile tubing 112 and into the conditioning chamber 7. In the conditioning chamber 7, the liquid undergoes sterilization by means of an ultraviolet (UV) lamp 4, and foam fractionation by fine gas bubbles 6 discharged from block bubbler 13, which can for example be airstone or limewood. The high surface area of these fine bubbles promote the removal of amphipathic molecules such as proteinaceous contaminants by concentration of the contaminants in the overlying foam. Gas is provided by gas cylinder 118, regulator 15 and gas addition line 120. Oxygenation and pH balancing can also occur depending on the gas and liquid used. When using an artificial CSF containing a 10 mM concentration of bicarbonate, for example, a mixture of 95% oxygen and 5% carbon dioxide gas can be used to both oxygenate the liquid and generate a physiologic pH by means of the interaction of bicarbonate in the liquid and carbon dioxide in the gas (a process known as bicarbonate buffering). In the treatment of a malignant disorder, a low-oxygen environment or non-physiologic pH may be desired and can be accomplished by the appropriate selection of liquid and gas. The flow rate of the gas may be adjusted to the minimum gas flow required to produce a substantial stream of fine bubbles (usually less than 1 l/min). The overflow of concentrated foam and contaminants 160 is collected in partitioned area 3 of the chamber and conducted to a waste receptacle 124 through line 126.

Foam fractionation can be carried out by a variety of device configurations, all of which are intended to fall within the scope of the invention. In the preferred configuration the liquid is bubbled by means of an airstone or limewood block and the contaminant-laden foam generated by the interaction of the stream of bubbles and dissolved contaminants in the liquid is separated from the liquid as it overflows into a waste container. Alternatively, the foam can be directed into an elevated chimney arrangement in which the continual accumulation of foam due to the bubble stream causes it to overflow into a waste receptacle. Another alternative is to separate the foam from the liquid by applying suction to the foam. The foam itself may be generated by a number of means. The foaming action can be made to occur by spraying the liquid at high velocity over a series of obstacles in a chamber, or by violent mixing of, the liquid with the air or gas in a chamber using an impeller, or by drawing a mixture of liquid and gas into a Venturi tube.

Liquid leaving the chamber passes around the baffles into exit portion 17, and then passes through tubing 128 from portion 17 of the chamber through pump 16 and sterile tubing 130 to end 8B of catheter 8. It then passes through the inflow barrel 19 of the catheter 8 into the body cavity. Continuous alimentation of the system with fresh biocompatible liquid from an elevated receptacle 9 is accomplished via passage of fresh liquid through a drip chamber 11 and tubing 132 connected to the chamber 7. The preferred rate of alimentation with fresh liquid is 100-150 ml/h. For larger cavities with greater liquid absorption, such as the peritoneum, a faster rate may be required. The addition of external liquid to the system provides a means of ensuring adequate liquid levels in the chamber 7, and also of adding drugs, modulating the composition of the recirculated liquid, diluting contaminants, and driving the overflow of contaminant-laden foam toward the waste receptacle 10. Liquid flow direction through the chamber 7 is preferably reversible, thereby permitting the primary catheter pumps 5 and 16 to be reversed in the case of a blockage condition should one occur.

Many different liquids can be used with the apparatus of the invention. In the case of body cavities which already contain substantial quantities of a naturally occurring liquid, such as the cerebrospinal fluid of the central nervous system, this naturally occurring liquid can be drawn out of the cavity and mixed with a quantity of artificially manufactured cerebrospinal fluid substitute. The mixture of the naturally occurring liquid and the artificial substitute is then recirculated within the cavities containing the brain and spinal cord to achieve the desired temperatures and pressures within the cavity. A variety of such artificial cerebrospinal fluids and the means to manufacture them are well known in the scientific literature. As another example, the peritoneal fluid which occurs naturally in the peritoneal cavity of the abdomen can be drawn from that cavity and mixed with artificial saline. This mixture is then recirculated within the cavity. In the case of treatment of a malignancy, the saline or other biocompatible liquid can contain chemotherapeutic agents. Cavities containing little or no endogenous liquids, such as the mediastinum of the chest, can simply be infused with saline or other biocompatible liquid, which can then recirculated to achieve the desired temperature and pressure over the desired time period.

Pressure and temperature are continuously monitored by means of sensors mounted on the primary catheter 8 as described with respect to sensor package 21. In the preferred embodiment, the strain gauge sensor 171 is referenced against atmospheric pressure to measure intracavity pressure. It and the thermocouple are conveniently present as part of a sensor package 21 (FIG. 8B). Other sensor technologies are available for the measurement of pressure and temperature, including the use of fiberoptic interferometry, and are intended to fall within the scope of the invention. The readings from these sensors (and optional sensor 102) are displayed on monitor 142 and optionally are inputs to the computer 141 for automated process control. In an automated control embodiment, computer 141 controls regulator 15, heater 14, ultraviolet sterilizer 4, and pumps 5 and 16 as shown diagrammatically by dashed control lines 190. Optionally, burette 2 and drip unit 11 can be replaced with automatic liquid supply regulating apparatus for automated control of liquid supply if desired.

The close proximity of the inflow and outflow ports at the tip of 8A the primary catheter 8 implies that a portion of the inflow liquid will be immediately drawn into the outflow port within the cavity. Nevertheless, a dispersion rate on the order of 50% of temperature-controlled liquid away from the catheter will occur, and the flow rate can be increased over a broad range without creating harmful pressure differentials. If desired, the primary catheter can be replaced with two separate catheters, which replace barrels 18 and 19 respectively, located in close proximity to one another. This is not preferred, however, because the risk of injury and infection is increased when two catheters are implanted instead of one.

The optional secondary catheter 1 is preferably a single-lumen catheter which may be inserted in the body cavity 35 in a location 36 that is distant from the area of insertion of the primary catheter, to drain liquid into the conditioning chamber. The purpose of this optional catheter is to draw liquid from the area of the body cavity near the primary catheter, where temperature control is easiest to maintain by pumps 5 and 16, toward an extremity of the cavity where temperature would otherwise be poorly controlled. If the primary catheter is positioned in the ventricles of the brain, for example, the secondary catheter can be positioned in the lumbar cistern (a CSF-containing space in the low back) to draw temperature-controlled liquid over the spinal cord. The temperature of the liquid in the secondary catheter is measured by a sensor positioned either within the catheter itself (as in the preferred embodiment at 102), or at another point such as the point at which the liquid is discharged into the chamber.

The flow through the secondary catheter may be regulated by means of a standard lumbar drain arrangement in which the liquid is conducted to a burette 11 positioned at a fixed height above the patient. The height H of the placement of the burette determines the pressure head which must be overcome before the catheter drains. Drainage from the burette is then conducted back to the conditioning chamber by gravity. In this arrangement, given a positive pressure within the body cavity, the height of the drain kit may be lowered to increase the rate of flow through the secondary catheter until the desired temperature of the drained liquid, and, by inference, within the extremity of the body cavity, is achieved. In another embodiment of the invention, the secondary catheter can be drained by means of a pump 134 (shown in phantom) in line 132. In this embodiment pump 134 is feedback-controlled based on the temperature of the drained liquid. It can also be controlled from the computer by control line 191.

Pumps 5 and 16 (and 134 if present) can be any suitable pumps for the pumping of sterile liquid. In the preferred embodiment, the pumps are peristaltic tubing pumps driven by electric motors which can be controlled by computer 141.

Chamber 7 is cooled or heated to a desired temperature by means of heating and/or cooling means 14. In the preferred embodiment, means 14 is a solid state chiller/heater device which makes use of Peltier elements to cool or heat the walls of the chamber 7. However, the particular heating and cooling means are not critical, and can be combined or separate. For example, units using compressor-based refrigeration and electric resistance heaters can be used. Depending on the use to which the apparatus is to be put, there can be only heating means, or only cooling means, or both heating and cooling means present.

FIG. 2A shows a close view of the insertion tip 8A of the primary catheter 8. The lumen 18 removes liquid from the cavity, while the lumen 19 infuses liquid into the cavity. Orifices 20 are cut into the tip and open from the lumens to the cavity. Each of the lumens is D-shaped, so that the overall cross-section of the catheter 8 is cylindrical. The diameter of the catheter shaft is preferably on the order of 5 mm for placement in the central nervous system, but may be larger for use in other body cavities. Other catheter geometries with two lumens for conducting inflow and outflow, including coaxial lumens, and variations of the tip apertures are also intended to fall within the scope of the invention. Optionally, two separate catheters can be used instead of a double-barreled catheter.

Figure 2B:
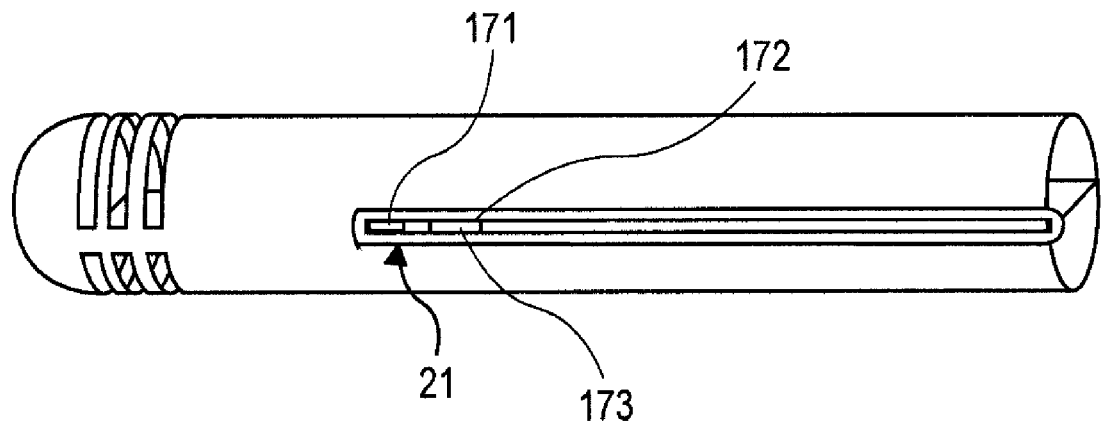
FIG. 2B is a further view of the preferred catheter tip, showing a microsensor package mounted in a longitudinal groove.

FIG. 2B shows a view of the insertion tip 8A and a portion of the shaft of the primary catheter 8. Sensor package 21 is positioned in a longitudinal groove in the shaft. The sensor package 21 monitors pressure using a strain gauge device 171 and temperature using a thermocouple device 172. The thermocouple sensor 173 is positioned away from the catheter wall such that it measures primarily the temperature of the environment outside the catheter but within the body cavity, rather than the temperature of the catheter wall.

Control of Temperature and Pressure

The temperature within the cavity is a function of the overall flow rate between the inflow and outflow barrels of the primary catheter 8 within the cavity, the rate of heat removal or addition to the recirculating liquid by the chiller/heater 14, and the rate of perfusion of the cavity contents by blood. In general, the greater the flow through the primary catheter, the more closely will the intra-cavity temperature approach that of the liquid in the conditioning chamber. In the preferred embodiment of the invention, the rate of pumping of liquid out of the cavity by the outflow pump 5 is feedback-regulated to minimize the size of the difference between the intracavity temperature and the chamber temperature. Intracavity temperature itself is controlled by means of feedback to the outflow pump 5 rate and the rate of heating or cooling by the chiller/heater of the liquid in tank 7. Since the body cavities to which the invention will be applied are essentially closed systems, the overall flow rate can be set by fixing either the inflow rate or the outflow rate at a given value.

Intra-cavity pressure is a function of net liquid removed or added to the cavity. When inflow exceeds outflow, the pressure will rise. Conversely, when the inflow rate is less than the outflow, pressure will fall. Hence, in the presence of constant outflow, the inflow pump rate may be varied as part of feedback loop with intracavity pressure as the controlled variable and pump rate as the manipulated variable to produce the desired pressure within the cavity.

Compliance Monitoring

The disclosed invention allows for the automated measurement of compliance within a body cavity. Compliance is the change in pressure per unit of volume added to a cavity's contents, often expressed as the inverse of this ratio in units of ml/mmHg. In the intracranium, for example, normal compliance values are in the range 0.5-1.4 ml/mmHg. Compliance falls when organ swelling in response to injury occurs. Both high intracranial pressure and low compliance predict adverse outcome, but critical compliance changes tend to precede critical intracranial pressure changes, making compliance the preferred means of monitoring brain swelling. The disclosed invention can monitor compliance by periodically stopping both inflow and outflow, then delivering a known volume of liquid into the ventricle (running the inflow pump in the forward direction or the outflow pump in the reverse direction for a defined time at a defined rate) and recording the pressure response. Periodic compliance monitoring using reversed flow from the outflow pump has the additional benefit of periodically clearing the outflow port of the primary catheter of debris that may be drawn into this port by suction. Compliance monitoring is incorporated into the preferred embodiment of the invention as a means of monitoring effects on organs within a body cavity during rewarming, as some organs, such as the brain, are known to respond to rewarming with swelling due to reactive hyperemia. Decreased compliance during the rewarming process is used as a signal to slow or temporarily reverse the rate of rewarming.

Placement of the Catheters

Figure 3A:
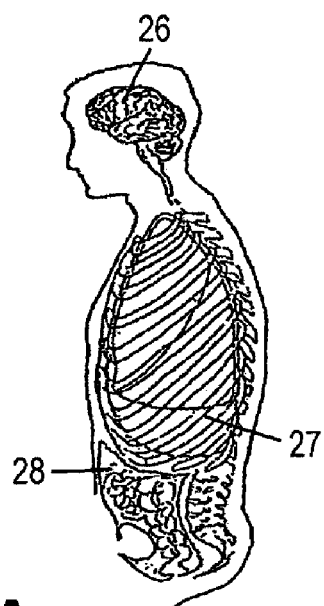
FIG. 3A is a schematic depiction of a human body, showing some of the anatomical sites in which a catheter according to the invention can be positioned.

FIG. 3 shows schematic anatomical diagrams of human head and torso in lateral transparent view depicting a variety of possible catheter placement sites for the primary catheter insertion tip 8A. FIG. 3A shows suitable placements in the peritoneum 28, the pleural space 27, and in the ventricular system (lateral ventricle preferred) of the brain 26. These are three important cavities in which continuous recirculation of a liquid at controlled temperatures and pressures with removal of contaminants and/or addition of drugs could be therapeutically useful. A solution of chemotherapy agents, for example, could be recirculated at these locations at a temperature higher than body temperature for the treatment of cancer. Catheter access (usually for the placement of passive drainage catheters) to each of these sites is routine for those skilled in the appropriate areas of medicine. Another cavity amenable to catheterization for this purpose is the mediastinum (not visible in FIG. 3). The catheter can also be placed in other body cavities where heating or cooling, or removal of contaminants or insertion of drugs is desirable.

Figure 3B:
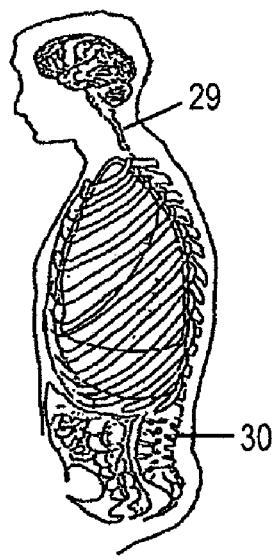
FIG. 3B depicts positioning of a primary catheter according to the invention in the C1-C2 subarachnoid space and the secondary catheter according to the invention in the lumbar cistern for spinal cord cooling.

FIG. 3B shows placement suitable for spinal cord injury. The insertion tip 8A of primary catheter 8 is depicted in the subarachnoid space at 29 C1-C2 (cervical vertebrae one and two, while the secondary drainage catheter 8 is located in the lumbar cistern 30. An artificial cerebrospinal solution at low temperature, for example, could be recirculated in these locations for hypothermic therapy in the case of spinal cord injury.

Figure 3C:
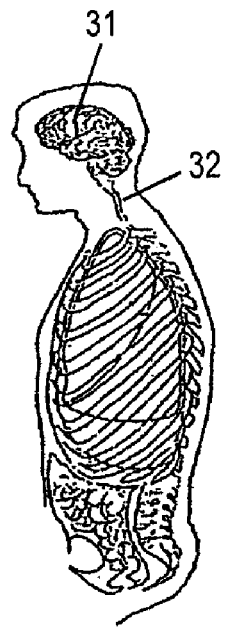
FIG. 3C depicts positioning of a primary catheter according to the invention in the lateral ventricle of the brain and the secondary catheter according to the invention in the C1-C2 subarachnoid space for brainstem cooling.

FIG. 3C depicts an arrangement in which the insertion tip 8A of the primary catheter 8 is inserted into one of the lateral ventricles at 31, while the secondary catheter 8 is inserted in the C1-C2 subarachnoid space at 32. This arrangement is intended to promote optimal temperature modulation in the distal brainstem and cerebellum by means of recirculated artificial cerebrospinal solution, for example, at low temperature. Automated Operation In a particularly desirable embodiment, automated control of the system is achieved by means of computer 141 running a program of feedback loops based on sensor inputs and control outputs. In the preferred automated embodiment, computer 141 provides the interface with the user and can download programmed instructions to the hardware via digital-to-analog/analog-to-digital (DAC/ADC) conversion as shown schematically at 190, 191.

Inputs to the control system include: the temperature and pressure in the body cavity (from sensors 171 and 173), the temperature of the liquid emerging from the secondary catheter (if present), from sensor 102, the temperature of the conditioning chamber (from thermocouple 105), the status of the chiller/heater unit 14, and the status of battery backup power supply (not shown, but preferred to be present). Outputs from the computer-based control system include: on/off, rate and pumping direction of the pumps 5 and 16 for the primary catheter, on/off, rate and pumping direction of the pump 13 for the secondary catheter (if present), and heat/cool and power level of the heating/cooling elements 14.

Feedback Loops

Several concurrent closed feedback loops are desirable for the automated operation of the system. In the preferred automated embodiment, these are PID (proportion integration derivative) tuned feedback loops. The following loops are disclosed:

1. Chiller/heater drive vs. intracavity temperature: In the preferred embodiment, the temperature of the liquid in the conditioning chamber is measured by means of a thermocouple sensor 105 in contact with the chamber. The temperature of the intracavity temperature as sensed at the primary catheter by thermocouple 173 serves as the controlled variable, while the cooling/heating activity of the chiller/heater 14 is the manipulated variable.

2. Outflow vs. intracavity-chamber temperature differential: Sufficient circulation of liquid between the conditioning chamber 7 and the cavity 35 is achieved when the temperatures at these two locations approach one another closely. Outflow from the primary catheter through barrel 18 is adjusted based on the difference in temperature between the cavity 35 and the chamber 7 such that flow is increased until this difference reaches a preset minimum. The controlled variable is the intracavity-chamber temperature difference, and the manipulated variable is the rate of the outflow pump 5.

3. Inflow vs. Pressure: Inflow from the primary catheter through barrel 19 is increased if the intra-cavity pressure is below the desired value and decreased if it is above the desired value. In the preferred embodiment, the controlled variable is intracavity pressure measured by strain gauge 171, while the manipulated variable is the rate of pump 16. An equivalent arrangement may obtained by reversing the roles of the pumps. A number of functionally equivalent schemes for the simultaneous control of temperature and pressure using the concept of bias flow or deltaflow (the difference between inflow and outflow rates) will be evident to one skilled in the art and are intended to be within the scope of the invention.

4. Outflow of the secondary catheter 1 vs. temperature of liquid emerging from the secondary catheter: Outflow from the optional secondary catheter is adjusted based on the temperature of the liquid as measured by sensor 102 at some point within the outflow pathway. The flow rate is increased until the temperature comes to within a desired range of the temperature at the primary catheter to ensure adequate distribution of liquid to the extremity of cavity in the region of the secondary catheter. In the preferred embodiment, the liquid temperature is measured within the secondary catheter at 102, and the flow rate is manually controlled by raising or lowering a gravity-based drain kit 2. An automated version of this control loop is disclosed in which the flow rate through the secondary catheter is controlled by means of a pump 132. In the automated version, drain kit 2 is removed.

Temperature/Pressure Control Profiles

The automated system can execute a defined sequence of temperature and pressure manipulations over long periods (hours to days) according to preset or user-defined temperature and pressure profiles.

Safety Features

A number of safety features can be incorporated into the preferred embodiment of the automated system of the invention. Preferably, power to the system is backed up by means of an uninterruptible power supply (not shown) which can maintain the operation of critical systems in the event of temporary disconnection from or failure of the mains supply. In the event of a non-recoverable failure of the computer, control of the pumps can preferably be switched to manual operation.

Suitably, the control software preferably includes a blockage detection routine that monitors the cavity pressure for loss of pressure control (intracavity pressure outside preset limits) and tests the catheters individually by measuring the pressure response to small volumes of liquid removed or added to the cavity. If the expected changes in pressure do not occur (rise in pressure in response to liquid added or a fall in pressure in response to liquid removed), then a blockage condition at the catheter is diagnosed. Four blockage conditions may occur: blockage of the outflow lumen in the OUT direction, blockage of the outflow lumen in the IN direction, blockage of the inflow lumen in the OUT direction, and blockage of the inflow lumen in the IN direction. These conditions preferably trigger a clearance routine in which flow is temporarily reversed in the affected catheter to clear debris. Total blockage in both the IN and OUT direction of a lumen that fails to clear is a non-recoverable condition that triggers an alarm signaling the need for operator intervention. Pump motor failure or blockage of either inflow in both lumens or outflow in both lumens is also non-recoverable. Blockage of outflow in one lumen and/or inflow in the other, however, is recoverable by reversal of flow through the two lumens.

If desired, equipment and control systems can be twinned for further safety. Thus, two computerized control systems can be operated so that the failure of one can be compensated by the other, and or two chillers can be operated in parallel. Electrical contact circuits can also be used to monitor the connection status of the different parts of the system.

EXAMPLE

An arrangement as shown in FIG. 1 was used to remove cerebrospinal fluid and return a mixture of cerebrospinal fluid and artificial cerebrospinal fluid cooled to approximately 2° C. in an adolescent pig (40 lbs). The animal was intubated and monitored under general anaesthesia. Rectal body temperature was controlled at 37° C. using a heating pad. The primary catheter was inserted into the right lateral ventricle while a temperature probe was inserted into the brain parenchyma on the opposite side of the brain (left parietooccipital region). The indicated flow rates were produced by varying the speed of the outflow pump 5 and intracranial pressure was adjusted by controlling the speed of the inflow pump 8.

Figure 4A:
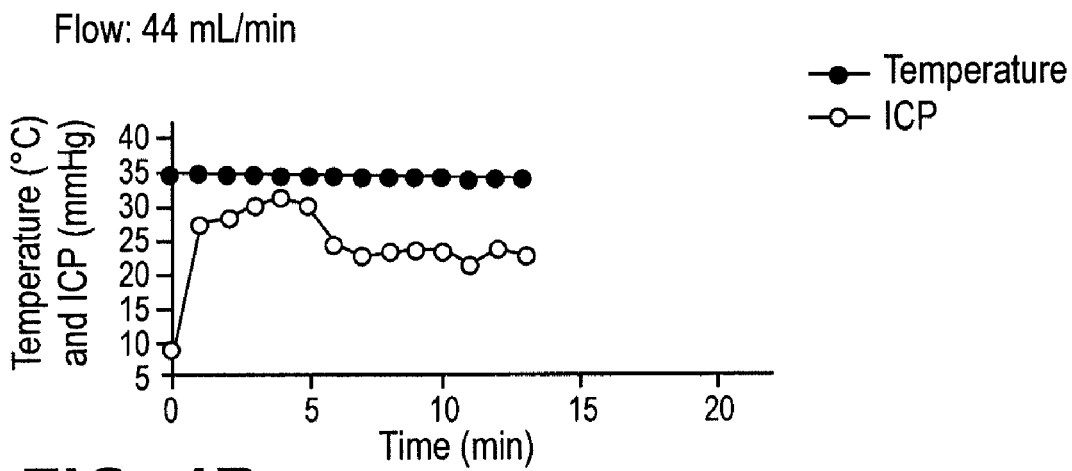
FIG. 4 is a graphical representation of brain temperature and pressure data collected using one embodiment of the apparatus of the invention in an anesthetized pig. It illustrates three different runs as FIGS. 4A, 4B, and 4C.
Figure 4B:
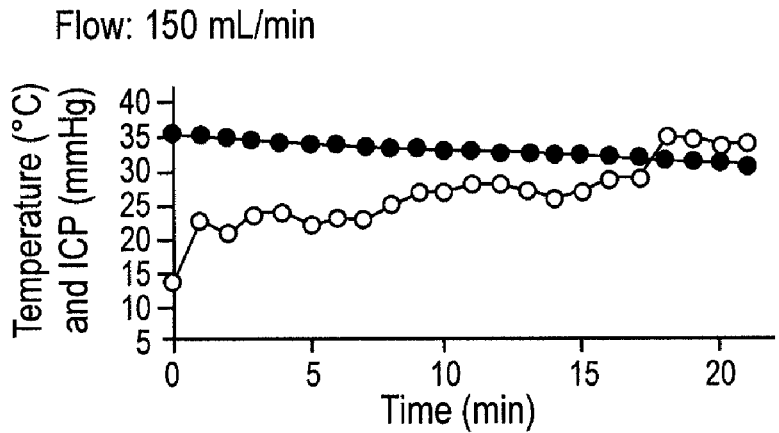
Figure 4C:
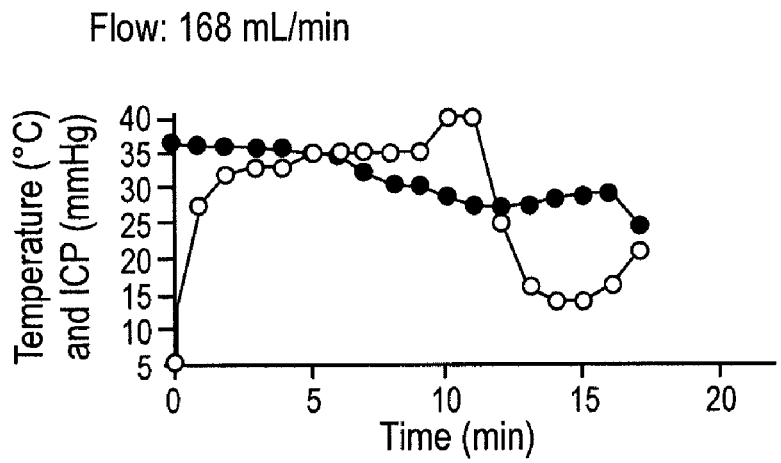

The results of three runs at different flow rates are presented in FIG. 4. For each run, the intracranial pressure (ICP) in millimeters of mercury is shown as white circles and the temperature of the left parietooccipital region of the brain in degrees Celsius is shown as black circles. The flow rates were FIG. 4A-44 mL/min, FIG. 4B 150 mL/min and FIG. 4C-168 mL/min. As shown, higher flow rates and greater ICP's led to faster brain cooling in the presence of normal rectal temperatures. Therapeutic temperatures (<33° C.) could be attained within 15 min without any perturbations in rectal body temperature. Indeed, in the third trial, the brain temperature dropped to 24 degrees Celsius in less than 20 minutes.

It will be understood that the present disclosure teaches presently preferred embodiments of the invention, and that modifications to such embodiments will be evident to one skilled in the art. Such modifications are intended to be within the scope of the invention, and the claims are to be read as including them.

What is claimed is:

1. Apparatus for modulating introduction and removal of a liquid within a cavity of a patient's body, the cavity comprising a cavity outside of blood vessels, the apparatus comprising:
   a catheter configured for insertion into the cavity and introduction and removal of liquid from the cavity;
   one or more sensors positionable in the patient's body so as to sense a condition of liquid in the cavity; and
   a controlled pumping system operatively coupled to both the catheter and the one or more sensors, the controlled pumping system configured to control introduction and removal of liquid from the cavity so as to maintain a selected liquid condition value.

2. The apparatus of claim 1, the catheter comprising a first lumen for introducing liquid into the cavity and a second lumen for removing fluid from the cavity.

3. The apparatus of claim 1, wherein the one or more sensors are positioned on the catheter.

4. The apparatus of claim 1, wherein the one or more sensors are positioned separate from the catheter and positionable at a location separate from the catheter.

5. The apparatus of claim 1 wherein the condition is liquid pressure.

6. The apparatus of claim 1 wherein the condition is liquid temperature.

7. The apparatus of claim 1 wherein the catheter comprises a dual lumen catheter.

8. The apparatus of claim 1, further comprising a first receptacle for storing liquid to be introduced into the patient's cavity and a second receptacle for collecting liquid removed from the patient's cavity.

9. The apparatus of claim 8, wherein the first receptacle and second receptacle are coupled so as to allow recirculation of liquid.

10. The apparatus of claim 1 further comprising a second catheter configured for removal of liquid from the cavity.

11. A feedback-controlled apparatus for introduction and removal of a liquid within a cavity of a patient's body, the cavity comprising a cavity outside of blood vessels, the apparatus comprising:
    a catheter configured for insertion into the cavity and introduction and removal of liquid from the cavity;
    one or more sensors positionable so as to sense a biological parameter of a patient's body; and
    a controlled pumping system operatively coupled to both the catheter and the one or more sensors, the controlled pumping system configured to modulate a property of the liquid in response to signals received from the one or more sensors and to maintain the biological parameter of the patient's body within a selected range.

12. The apparatus of claim 11, wherein the property of the liquid comprises rate of introduction or removal from the cavity.

13. The apparatus of claim 11, wherein the property of the liquid comprises contamination level, concentration, oxygenation, pH, or chemical agent or drug content.

14. The apparatus of claim 11 wherein the catheter comprises a dual lumen catheter.

15. A method of maintaining a liquid condition parameter within a body cavity other than a blood vessel within a patient's body, the method comprising:
    pumping liquid into the cavity;
    pumping liquid out of the cavity;
    monitoring a parameter of liquid within the cavity from a sensor disposed within the patient's body; and
    controlling at least one of liquid temperature, liquid pressure, and liquid flow rate in response to a liquid condition value measured in the monitoring step.

16. The method of claim 15 wherein the monitoring step comprises monitoring temperature of liquid within the cavity.

17. The method of claim 15 wherein the monitoring step comprises monitoring pressure of liquid within the cavity.

18. The method of claim 15 wherein the steps of pumping liquid into the cavity and pumping liquid out of the cavity comprises pumping liquids into and out of the cavity through a single catheter.

19. The method of claim 18 wherein the catheter comprises a dual lumen catheter.

20. The method of claim 15 wherein the step of pumping liquid out of the cavity comprises pumping liquid out of the cavity through an outflow catheter disposed remote from an inflow catheter through which liquid is pumped into the cavity.

* * * * *